United States Patent
Acevedo-Duncan et al.

(10) Patent No.: US 7,482,131 B2
(45) Date of Patent: Jan. 27, 2009

(54) DETECTION OF PKC-IOTA AS A BIOMARKER FOR BRAIN TUMORIGENESIS

(75) Inventors: Mildred Acevedo-Duncan, Plant City, FL (US); Rekha Patel, Valrico, FL (US)

(73) Assignees: United States Department of Veterans Affairs, Washington, DC (US); University of South Florida, Tampa, FL (US)

( * ) Notice: Subject to any disclaimer, the term of this patent is extended or adjusted under 35 U.S.C. 154(b) by 0 days.

(21) Appl. No.: 11/560,030

(22) Filed: Nov. 15, 2006

(65) Prior Publication Data

US 2007/0166733 A1 Jul. 19, 2007

Related U.S. Application Data

(60) Provisional application No. 60/736,764, filed on Nov. 15, 2005.

(51) Int. Cl.
*G01N 33/573* (2006.01)
(52) U.S. Cl. .......................................... 435/7.23; 435/6
(58) Field of Classification Search ....................... None
See application file for complete search history.

(56) References Cited

U.S. PATENT DOCUMENTS

2005/0112707 A1   5/2005  Altabeta et al.
2005/0227917 A1  10/2005  Williams et al.
2006/0185026 A1* 8/2006  Sacktor et al. ................ 800/12

OTHER PUBLICATIONS

Dermer, G.B. Bio/technology, 1994. vol. 12 p. 320.*
Freshney, R.I. Culture of Animal Cells, a manual of basic technique. Alan R. Liss, Inc. 1983, New York. p. 4.*
Baldwin, R.M., Garratt-Lalonde, M., Parolin, D.A.E., Krzyanowski, P.M., Andrade, M.A., and Lorimer, I.A.J. Protection of glioblastoma cells from cisplatin cytotoxicity via protein kinase Ci-mediated attenuation of p38 MAP kinase signaling. Oncogene, 2006. vol. 25, pp. 2909-2919.*
Fields, A.P. and Regala, R.P. Protein kinase Ci: human oncogene, prognostic marker and therapeutic target. Pharmaceutical Research, 2007. vol. 55, pp. 487-497.*

* cited by examiner

*Primary Examiner*—Misook Yu
(74) *Attorney, Agent, or Firm*—Thomas E. Toner; Smith & Hopen, P.A.

(57) ABSTRACT

A method of detecting brain tumorigenesis in a subject, the method including the steps of (a) obtaining a sample from the brain of the human subject, (b) detecting quantitatively or semi-quantitatively in the sample a level of expression for PKC-iota and (c) comparing the expression level in (b) to a level of expression in a normal control, wherein overexpression of PKC-iota, with respect to the control, indicates the presence of a glioma or meningioma in the subject. The present invention is based upon the discovery that PKC-iota levels are elevated during brain tumorigenesis. Furthermore, the proliferation rate of the tumor correlates with the level of PKC-iota. The invention also provides methods of treating gliomas and meningiomas by administering to the subject a compound that inhibits the expression of PKC-iota. The compound can be a small interfering RNA (siRNA) molecule.

7 Claims, 3 Drawing Sheets

A

DETECTION OF PKC-IOTA AS A BIOMARKER FOR BRAIN TUMORIGENESIS

CROSS REFERENCE TO RELATED APPLICATIONS

This application claims priority to currently pending U.S. Provisional Patent Application 60/736,764 entitled, "Detection of PKC-iota as a Biomarker for Brain Tumorigenesis", filed Nov. 15, 2005, the contents of which are herein incorporated by reference.

FIELD OF INVENTION

This invention relates to detection and treatment of brain tumors. More specifically, this invention relates to use of PKC-iota in the detection of brain tumorigenesis and methods of inhibiting the expression and activity of PKC-iota as a treatment for brain tumorigenesis.

BACKGROUND OF THE INVENTION

Protein kinase C (PKC) is a family of fourteen known isozymes found in varying ratios in the cytosolic and membrane fractions of cells, depending on the type of tissue and its physiological state (Nishizuka 1992 Science 258, 607.). PKC isozymes can be classified into three groups. Group I includes $Ca^{2+}$ dependent isozymes: cPKC-alpha, cPKC-betaI cPKC-betaII and cPKC-gamma. Isozymes in group II, nPKC-epsilon, nPKC-delta, nPKC-eta and nPKC-theta are $Ca^{2+}$ independent. Group III includes the atypical PKC: aPKC-iota (Selbie et al. 1993 *J. Biol. Chem.* 268, 24296), aPKC-zeta, aPKC-zetaI (Hirai et al. 2003 *Neuroscience Lett.* 348, 151), aPKC-mu (protein kinase D) and aPKC-nu (Hayashi et al. 1999 *Biochim. et Biophys. Acta.* 1450, 99) which are insensitive to both diacylglycerol and calcium and neither bind to nor are activated by phorbol esters. PKC regulates cellular functions, metabolism and proliferation by phosphorylating proteins in response to transmembrane signals from hormones, growth factors, neuro-transmitters and pharmacological agents.

Of special interest is atypical PKC-iota which does not contain a $Ca^{2+}$-binding region, has one zinc finger-like motif and is the human homolog of the mouse PKC-lambda (Diaz-Meco et al. 1996 *Molec and Cell Bio* 16, 105). PKC-iota may play a role cellular malignancy as shown by its association with the transformed phenotype of human melanomas in vivo and in vitro (Selzer et al. 2002 *Melanoma Research* 12, 201) and by demonstrating that PKC-iota protects cells against drug induced apoptosis (Murray & Fields 1997 *J. Biol. Chem.* 272, 27521, Xie et al. 2000 *Mol. Brain. Res.* 82,107). In human lung cancer cells, PKC-iota is a Bad kinase that can phosphorylate and inactivate the proapoptotic BH3 protein leading to enhanced survival and chemoresistance (Jin et al. 2005).

The current method of detecting brain tumorigenesis is through biopsy and evaluation of tissue histology. It would be highly desirable to have a biomarker for the detection of brain tumorigenesis. Furthermore, it would be highly desirable to have a screening methodology to evaluate the proliferation rate of the detected tumor. Additionally, it would be highly desirable to have additional treatment regimens targeting the biochemical processes associated with tumorigenesis. The present invention provides systems and associated methodologies addressing these important needs.

SUMMARY OF INVENTION

In accordance with the present invention is provided a method of detecting brain tumorigenesis in a subject, the method including the steps of (a) obtaining a sample from the brain of the human subject, (b) detecting quantitatively or semi-quantitatively in the sample a level of expression for PKC-iota and (c) comparing the expression level in (b) to a level of expression in a normal control, wherein overexpression of PKC-iota, with respect to the control, indicates the presence of a glioma or meningioma in the subject. In certain embodiments the step of detecting detects the quantitative level of expression of PKC-iota in a sample tissue. The relative level of expression of PKC-iota in the sample as compared to the control correlates with the proliferation rate of the tumor. In further embodiments the comparing step can include the steps of contacting a protein sample from the brain of the subject with an antibody which recognizes PKC-iota protein and detecting the complex between the antibody and the PKC-iota protein. In this manner the PKC-iota protein within the tissue sample is assayed. The antibody used in the contacting step can be a monoclonal antibody or a polyclonal antibody. The method can be used in an immunoassay including a radioimmunoassay, Western blot assay, immunofluorescent assay, enzyme immunoassay, immuno-precipitation, chemiluminescent assay, immunohistochemical assay, dot blot assay and slot blot assay. In an advantageous embodiment the immunoassay is a Western blot assay.

The present invention further provides a method of diagnosing the presence of a glioma or meningioma in a subject including the steps of (a) obtaining a sample from the brain of the human subject, (b) detecting quantitatively or semi-quantitatively in the sample a level of expression for PKC-iota protein or PKC-iota-specific mRNA and (c) comparing the expression level in (b) to a level of expression in a normal control, wherein overexpression of PKC-iota protein or PKC-iota-specific mRNA, with respect to the control, indicates the presence of glioma or meningioma in the subject. In certain embodiments the step of detecting detects the quantitative level of expression of PKC-iota in a sample tissue. The relative level of expression of PKC-iota in the sample as compared to the control correlates with the proliferation rate of the tumor.

In still further aspects the present invention provides a diagnostic kit for the detection of brain tumorigenesis. The diagnostic kit includes, in combination, an anti-PKC-iota antibody, a labeled secondary antibody capable of immunocomplexing with the anti-PKC-iota antibody, a positive control derived from a tissue sample of a brain tumor and a negative control derived from a normal brain tissue sample. The kit can further include a suitable diluent for the brain tissue sample to be tested. The label of the secondary antibody can be a fluorescent label, an enzyme label and a radioactive label.

In still another aspect the present invention provides a method of treating a brain tumor in a subject comprising the step of administering to the subject a compound that inhibits the expression of PKC-iota. The compound can be a small interfering RNA (siRNA) molecule. In an advantageous embodiment the siRNA molecule includes a sequence comprising at least one of SEQ ID NO: 1, SEQ ID NO: 2 or SEQ ID NO: 3.

The present invention further provides a method of inhibiting expression of human PKC-iota mRNA comprising administering to a subject an effective amount of an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human PKC-iota mRNA such that the human PKC-iota mRNA is degraded. The siRNA can be administered in conjunction with a delivery reagent. The delivery agent can be lipofectin, lipofectamine, cellfectin, polycations, or liposomes. The method can be used in a subject being treated for a glioma or meningioma.

BRIEF DESCRIPTION OF THE DRAWINGS

For a fuller understanding of the invention, reference should be made to the following detailed description, taken in connection with the accompanying drawings, in which:

FIG. 1A illustrates a Western blot showing detection of PKC-iota in benign and malignant meningiomas and gliomas, but not normal brain tissue. FIG. 1B is a histogram graphically depicting the results of the Western blots.

BRIEF DESCRIPTION OF SEQUENCES

Figure 1:
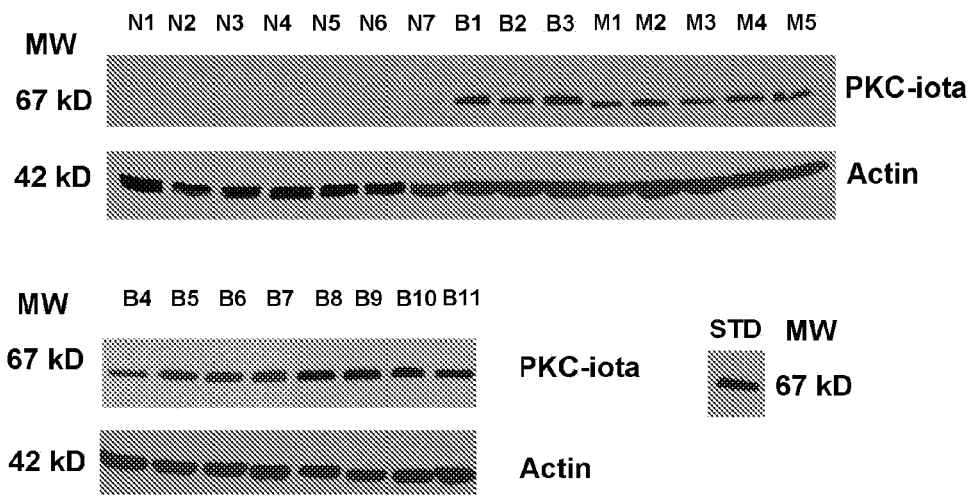
FIG. 1 illustrates that PKC-iota is present in benign and malignant meningiomas, gliomas but not normal brain tissue.
Figure 1:
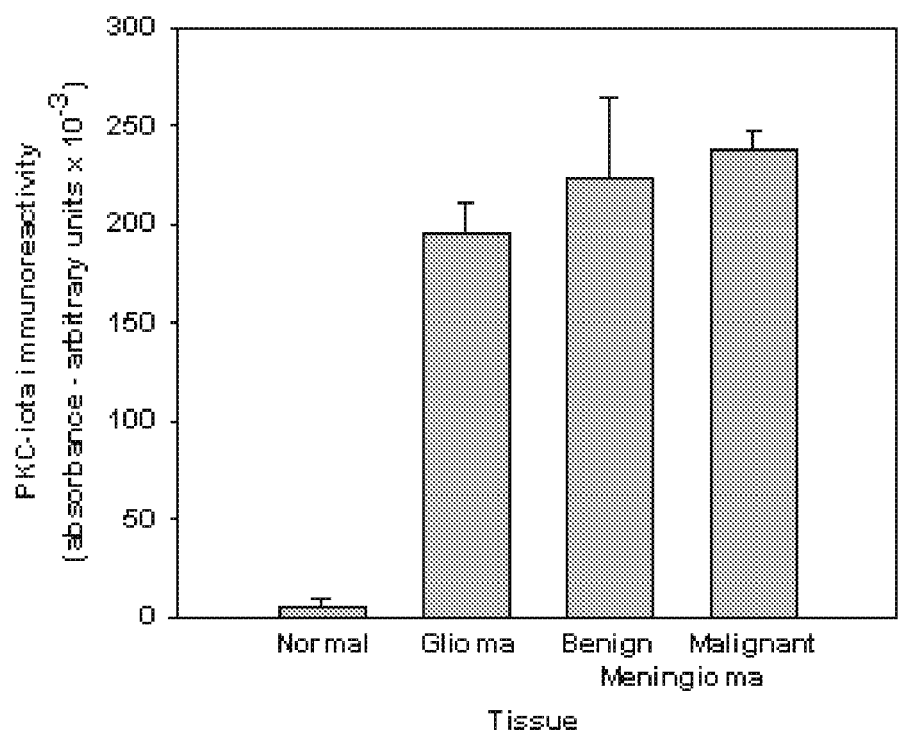

```
                   SEQUENCE LISTING

<110> Acevedo-Duncan, Mildred
<120> Detection of PKC iota as a Biomarker
      for Brain Tumorigenesis
<130> 1372.383.PRC
<150> 60/736,764
<151> 2005-11-15
<160> 3
<170> PatentIn version 3.3

<210> 1
<211> 19
<212> RNA
<213> Artificial
<220>
<223> small inhibiting RNA sequence for PKC iota

<400> 1
uguugaaacg cuuggcuug                                19

<210> 2
<211> 19
<212> RNA
<213> Artificial
<220>
<223> small inhibiting RNA sequence for PKC iota

<400> 2
augacaaccc aaucguucc                                19

<210> 3
<211> 19
<212> RNA
<213> Artificial
<220>
<223> small inhibiting RNA for PKC iota

<400> 3
uacaagagaa gauauuggg                                19
```

DETAILED DESCRIPTION OF THE PREFERRED EMBODIMENT

The present invention is based upon the discovery that PKC-iota levels are elevated during brain tumorigenesis. Furthermore, the proliferation rate of the tumor correlates with the level of PKC-iota. Thus, in a first aspect the present invention provides a method of detecting, both qualitatively and quantitatively, brain tumorigenesis by assaying levels of PKC-iota.

Atypical protein kinase C-iota (PKC-iota) protects cells against apoptosis and may play a role in cell transformation. However, the in-vivo status and function of PKC-iota in human normal brain tissue, gliomas, benign and malignant meningiomas as well as its in-vitro status in proliferating and confluent glioma cells remains a subject of interest. The objectives of our research were to determine if expression of PKC-iota is altered in normal brain compared to either gliomas, benign or malignant meningiomas. Moreover, we wished to establish the expression of PKC-iota in proliferating and cell cycle arrested glioma cell lines as well as the effects of PKC-iota siRNA on PKC-iota protein content and proliferation. Western blots probing for PKC-iota were performed on 12 normal brain biopsies, 15 benign meningiomas, 3 malignant meningiomas and 2 gliomas. Results demonstrated no (n=9) or very weak (n=3) detection of PKC-iota in normal brain tissue. In comparison, PKC-iota was robustly present in the majority of the benign meningiomas. Similarly, PKC-iota was abundantly detected in all malignant meningiomas and gliomas. Western blotting for PKC-iota in confluent or proliferating glioma cell lines depicted robust quantities of PKC-iota in proliferating T98G and U-138 glioma cells. In contrast, confluent cells had either 71% (T98G) or 21% (U-138) less PKC-iota than proliferating cells. T98 and U-138 glioma cells treated with 100 nM PKC-iota siRNA had decreased proliferation compared to control siRNA-A and complete down-regulation PKC-iota protein content. These results support the concept that PKC-iota may be required for cell proliferation and promotes the possibility of utilizing PKC-iota detection as a marker for tumorigenesis.

In this study we examined the PKC-iota protein content in normal brain biopsies, gliomas, benign and malignant meningiomas as judged by Western blotting. Of interest were the results depicting increases in PKC-iota abundance in benign or malignant meningiomas and gliomas compared to normal brain tissue. The results from this study indicate that PKC-iota is a marker for brain tumorigenesis. We also investigated the effects of PKC-iota siRNA on T98G and U-138 glioma cell lines. Results demonstrated that PKC-iota siRNA reduced PKC-iota protein content concomitantly with a decrease in glioma cell proliferation. Taken together, these results suggest that PKC-iota may play a role in glioma cell proliferation and tumorigenesis.

The invention is described below in examples which are intended to further describe the invention without limitation to its scope.

EXAMPLE 1

PKC-iota is involved in the transition of normal to pre-malignant and malignant lesions.

The relationship between the absence of PKC-iota in normal brain tissue and its robust presence in either benign/malignant meningiomas or gliomas is summarized in Table 1. Western blots probing for PKC-iota in 12 normal brain biopsies, 15 benign meningiomas, and 5 malignant tumors revealed a complete absence (n=9) or very low detection (n=3) of PKC-iota in normal brain tissue (Table 1). In comparison, PKC-iota was robustly present in the majority of the benign meningiomas (n=14) and only weakly present in one. Similarly, PKC-iota was abundantly detected in all malignant meningiomas (n=3) and gliomas (n=2). Western blots corresponding to some of the data present in Table 1 are shown in FIG. 1A. PKC-iota in was identified in Western blots by a band with a molecular weight of 67 kD, which corresponded to the immunoreactive signal obtained from U-373MG glioma cells which contain PKC-iota. As a control, Westerns blots for PKC-βII did not show a pattern of expression specific to either normal brain tissue, benign or malignant brain tumors (data not shown). Control actin Western blots showed actin immunoreactive bands at a molecular weight of 42 kD. The actin immunoreactive bands were of equal intensity indicating that equal amount of protein were loaded into each lane. Human autopsy derived normal brain tissue (N1, frontal lobe; N2, cortex; N3 and N4 unspecified brain; N5, cortex; N6, cerebellum), benign tumor tissue (B1, B4, B7, B9 and B10 [WHO grade 1] meningothelial meningioma; B3, B5, B8, meningioma; B6 fibroblastic meningioma; B2, B11, fibrous meningioma [WHO grade 1], and malignant tumor tissue, M1, M4 [WHO grade IV] glioblastoma multiforme; M2, right frontal lobe meningioma; M3, atypical meningioma [WHO grade II]; M5, anaplastic meningioma [WHO grade III]). Specimens were obtained from the Cooperative Human Tissue Network. Brain tissue proteins lysate (50 μg) were subjected to gel electophoresis and Western blotting was performed with monoclonal antibodies against PKC-iota (cat. # 610176, BD Transduction, San Diego, Calif.) at a 1:2000 dilution (5 μg). Secondary antibodies were obtained from Accurate JOM035146, Westbury, N.Y.) and used at 1.5:10000 dilution (48 μg). Western blots were probed for actin with a goat polyclonal antibody to actin (SC-1616) at a 2.5:2000 dilution (10 μg) and secondary antibodies SC-2350 at a 1:2000 dilution (8 μg, Santa Cruz Biotechnology). Positive control for PKC-iota immunoreactivity was U-373MG cell lysate (81 μg) which contains PKC-iota.

The data presented in Table 1 and FIG. 1A are also graphed in FIG. 1B which depicts 38-46 fold increase in PKC-iota immunoreactivity in glioma, benign and malignant menigiomas when compared to normal brain tissue. Immunoblots from 12 normal brain specimens, 2 gliomas, 15 benign meningiomas and 3 malignant meningiomas were quantitated, and the mean plus and minus the SE value is presented for each tissue type. Bars comparing normal tissue with either glioma, benign or malignant meningioma differ according to Tukey's Honestly Significant Difference Test (P=0.001). This data was subjected to analysis of variance and mean separation was by Tukey's Honestly Significant Difference Test (Minitab, Inc., State College, Pa.). The level of PKC-iota in normal brain tissue differed from that in gliomas, benign or malignant meningiomas (P=0.001). There was no significant difference (P>0.05) in PKC-iota immunoreactivity between gliomas, benign and malignant meninigiomas. This study demonstrates that PKC-iota is overexpressed in glioma, benign and malignant meningiomas but not in normal brain tissues. These results provide support for the involvement of PKC-iota in the transition of normal to pre-malignant and malignant lesions.

TABLE 1

Status of PKC-iota in brain tissues, meningiomas and gliomas*

| Tissue Type | Not Present | Weakly Present | Positively Present |
|---|---|---|---|
| Normal brain | 9 | 3 | 0 |
| Glioma | 0 | 0 | 2 |
| Benign Meningioma | 0 | 1 | 14 |
| Malignant Meningioma | 0 | 0 | 2 |

*Normal brain tissue was obtained from frontal lobe, brain cortex, cerebellum, hippocampus, pons, corpus collosum, or basal ganglia. Benign tumor were meningiomas. Malignant tumors were either meningiomas or gliomas

EXAMPLE 2

Role of PKC-Iota in Cell Cycle Progression.

Figure 2:
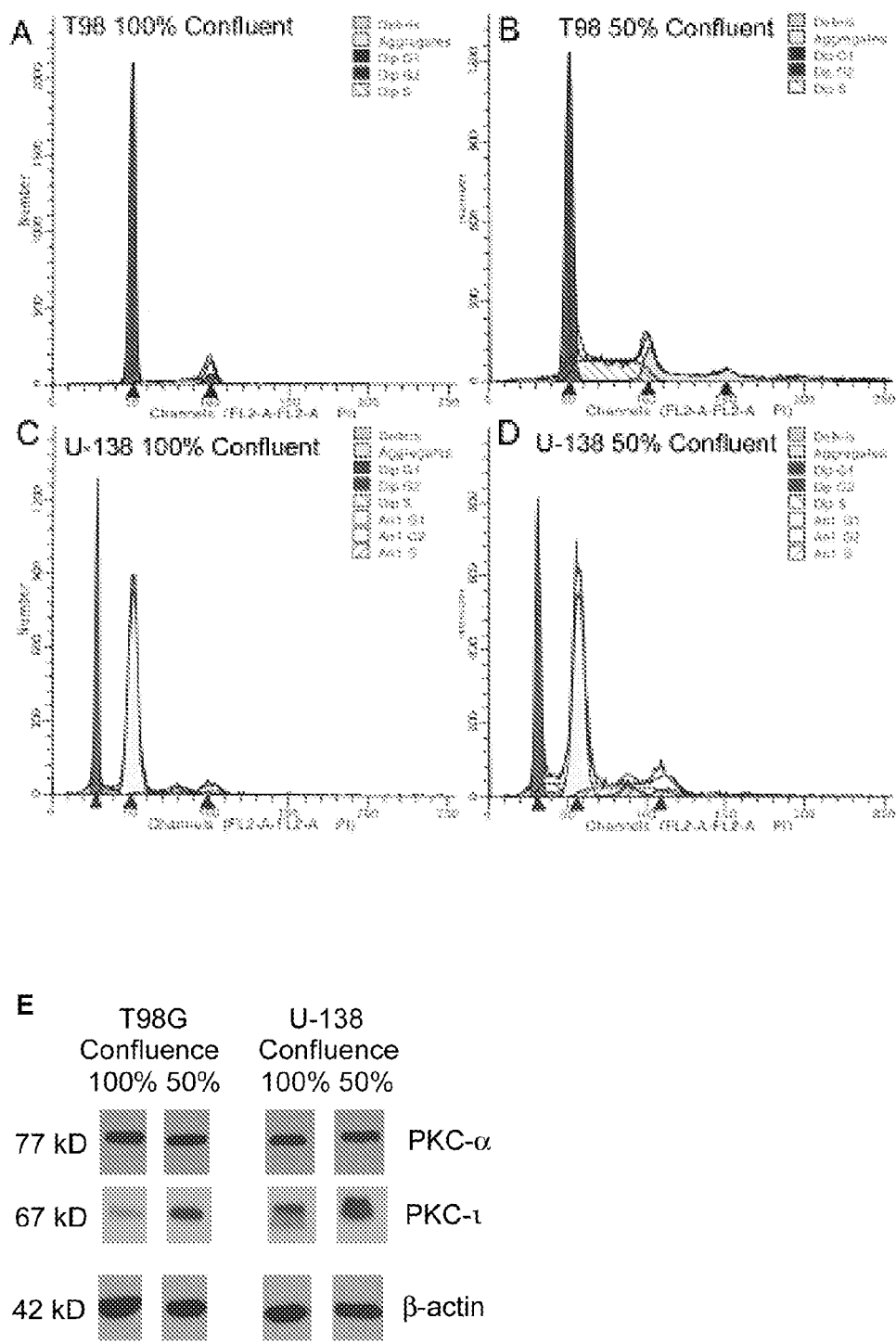
FIG. 2 illustrates the effects of cell density and cell cycle progression on PKC-iota concentration in T98G and U-138 glioma cells. FACS analysis of DNA content in 100% confluent T98G (A) or U-138 cells (C) and 50% confluent T98G (B) or U-138 (D) cells. U-138 glioma cells are aneuploid. U-138 DNA histograms are from one representative experiment and illustrate two cycling populations with a $G_0/G_1$ peak at 2N (dark shaded peak) and another at 4N (light shaded peak). Total DNA content for $G_0/G_1$, DNA synthesis phase (S) and gap2 and mitosis ($G_2M$) was quantified by addition of each of the phases in both populations. Forty thousand events were collected per time point and treatment group. Western blots of PKC-iota present in T98 or U-138 cells which were at different stages of confluence (E). Duplicate cultures from the flow cytometry experiment were harvested at the indicated times and prepared for Western blots. Equal amounts of cellular protein (20 μg) were loaded per well. Anti PKC-α (Santa Cruz Biotechnology; SC-8393) was used at a 1:1300 dilution (3 μg). Anti-PKC-iota (P20520; Transduction Lab., Lex., Ky.) was used at 1:12000 dilutions (0.83 μg). Western blots were also performed to verify that protein loading (20 μg) and protein integrity are equal. Western blots were probed with a monoclonal antibody to actin (Santa Cruz Biotechnology; SC-8432) at a 5:1000 dilution (40 μg). Secondary antibodies were obtained from Accurate (JGM035146, Westboro, N.Y.) and used at 1:15000 dilutions (1 μg). Band intensity of PKC-iota in T98G (F) and U-138 (G) was quantified by densitometry.

To establish if PKC-iota plays a role in cell cycle progression, T98G and U-138 glioma cells were plated and samples taken for flow cytometry or Western blotting when cells were either serum starved for 48 h and were 100% confluent, or when cells were 50% confluent and not serum starved. T98G cells and U-138 glioma cells which were 100% confluent had 94% and 74% of the cells in quiescence/Gap 1 ($G_0/G_1$), respectively (FIG. 2A, 2C and Table 1). In contrast, rapidly dividing 50% confluent T98G cells had 64% of the cells accumulated in $G_0/G_1$ and in U-138 glioma cells 54% were $G_0/G_1$ phase (FIG. 2B, 2D). Western blotting for PKC-iota in these cell populations depicted robust quantities of PKC-iota in proliferating 50% confluent T98G and U-138 glioma cells. In contrast, 100% confluent cells had either 71% (T98G) or 47% (U-138) less PKC-iota than 50% confluent cells (FIG. 2E, 2F, 2G). Differences between PKC-iota protein content in 100% confluent and 50% confluent rapidly proliferating cells was significant at P>0.05 (n=3). To establish that the variations in PKC-iota may be specific for PKC-iota we randomly selected to perform Western blots for PKC-alpha in confluent and proliferating cells. Westerns blots for PKC-alpha showed invariant levels of PKC-alpha in confluent and proliferating cells (FIG. 2 E) thereby suggesting that the results obtained with PKC-iota may be specific for PKC-iota and not other PKC isozymes. The one parameter that distinguishes T98G cells from fully transformed cells is that they behave similarly to normal cells by becoming arrested and stationary in $G_1$ phase (Stein 1979). These results depicting a relationship between cellular confluence and PKC-iota protein levels suggest that PKC-iota plays a role in cell cycle progression.

TABLE 2

Summary of Cell Cycle Phases*

| Cell Type | $G_0/G_1$ | S | $G_2M$ |
|---|---|---|---|
| 100% Confluent T98 | 94 +/− 1 | 4 +/− 3 | 2 +/− 3 |
| 50% Confluent T98 | 64 +/− 3 | 33 +/− 3 | 4 +/− 4 |
| 100% Confluent U-138 | 74 +/− 11 | 20 +/− 10 | 2 +/− 3 |
| 50% Confluent U-138 | 54 +/− 17 | 39 +/− 18 | 7 +/− 1 |

*N = 3 experiments per cell line.

EXAMPLE 3

Effects of PKC-iota siRNA on the proliferation of T98G and U-138 glioma cells and protein content.

Figure 3:
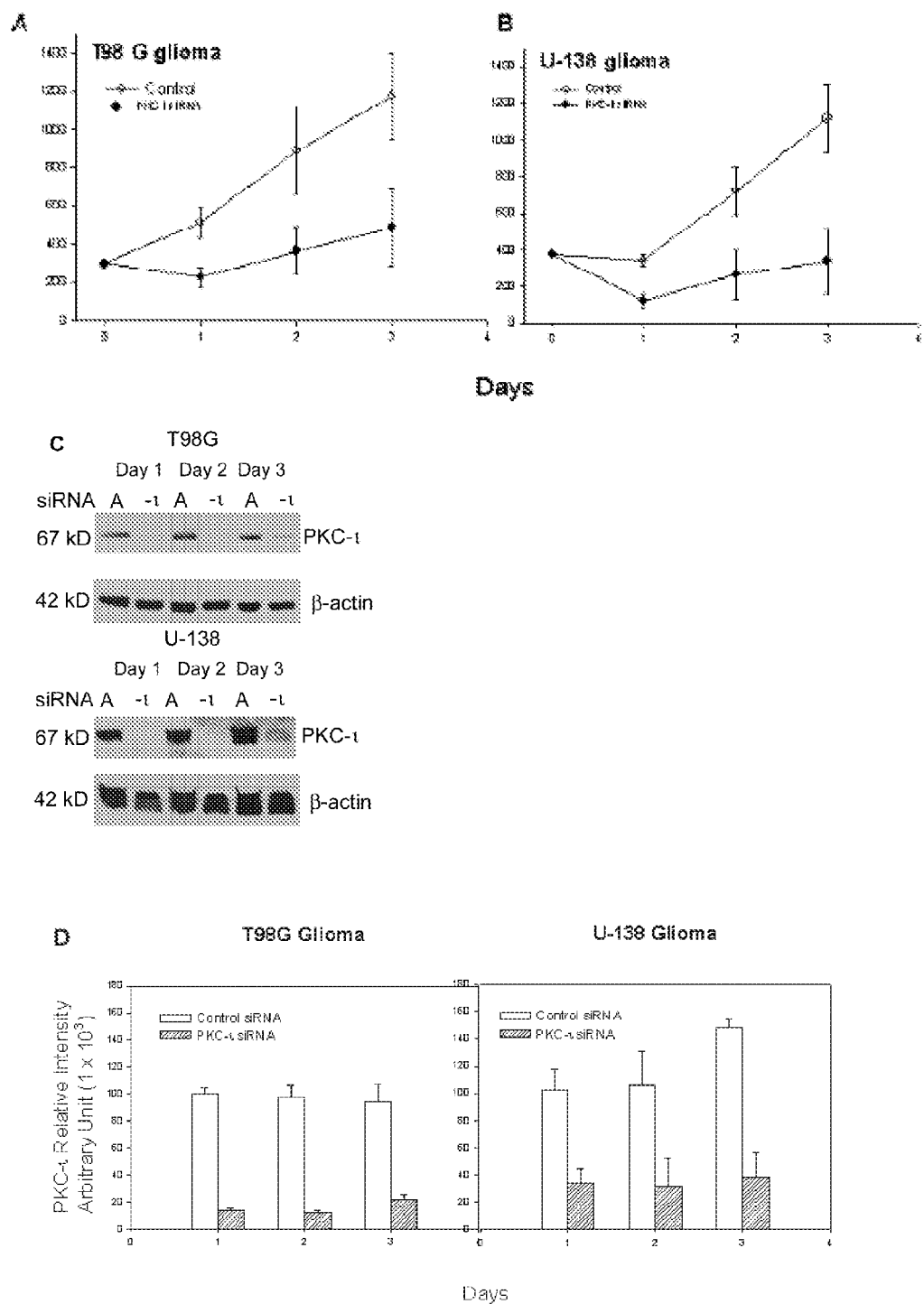
FIG. 3 illustrates the effects of PKC-iota siRNA on the proliferation of U-138 and T98G glioma cells and PKC-iota protein content. Cells were plated on 75 cm² flasks at a density of 3.75×10⁵ cells/flask. Twenty-four hours post plating, cells were incubated with either siRNA-A (100 nM; vehicle-control) or PKC-iota siRNA (100 nM) for 6 hours according to manufacture's instruction (Santa Cruz Biotechnology). During the 3-day incubation viable cells were quantified by trypan blue dye exclusion assay (A, T98G; B, U-138). Open symbols (O) represent control (siRNA-A) treated cells. Solid symbols (e) represent cells treated with PKC-iota siRNA (100 nM). Western blots of PKC-iota present in U-138 and T98G cells treated with PKC-iota siRNA (100 nM) at day 2 post treatment (C). The same cultures from the cell proliferation assays were harvested after counting and prepared for Western blots. Equal amounts of cellular protein (15 μg) were loaded per well. Anti-PKC-iota (P20520; Transduction Lab., Lex., Ky.) was used at 1:12000 dilution (0.83 μg). Western blots were also performed to verify that protein loading (15 μg) and protein integrity are equal. Western blots were probed with a monoclonal antibody to beta-actin (Santa Cruz Biotechnology; SC-8432) at a 5:1000 dilution (40 μg). Secondary antibodies were obtained from Accurate (JGM035146, Westboro, N.Y.) and used at 1:15000 dilutions (1 μg). Band intensity was quantified by densitometry (D). Data is representative of three experiments.

The effects of exposure to PKC-iota siRNA on T98 and U-138 glioma cell viability and proliferation was evaluated by Trypan blue dye exclusion (FIGS. 3A and 3B). Cell viability and number was counted 24-72 h following addition of either control short interfering RNAs (siRNA-A, vehicle control; 100 nM) or PKC-iota siRNA (100 nM) according to manufacture's instruction (Santa Cruz Biotechnology). Exposure of T98 or U-138 glioma cells to PKC-iota siRNA significantly reduce cell proliferation by 59% (P=0.002) and 69% (P=0.03), respectively at 72 h post treatment. Densitometric scanning of Westerns revealed that PKC-iota siRNA decreased PKC-iotaprotein content by 86% to 77% (T98G) and 66% to 74% (U-138) during the three day time course (FIG. 3C, 3D; n=3 experiments). Differences between PKC-iota protein content in control siRNA-A and PKC-iota siRNA treated cells was significant at P>0.05 for all time points. Control β-actin Western blots showed β-actin immunoreactive bands at a molecular weight of 42 kD. The actin immunoreactive bands were of equal intensity indicating that equal amount of protein were loaded into each lane. These results indicate that PKC-iota may be required for cell proliferation.

High grade malignant brain tumors are highly lethal tumors. Despite rigorous therapies, median survival is less than one year for patients with high grade tumors (Allalunis-Turner et al. 1992 *Int. J. Radiat. Onco. Biol. Phys.* 23, 339). While post operative radiation therapy clearly delays tumor regrowth and prolongs survival, total tumor control is rarely achieved. Glioma recurrence and radioresistance may be due to an abundance of hypoxic or tumor stem cells, rapid glioma proliferation, low radiosensitivity or the involvement of PKC isozymes in radiation resistance (Baumann et al. 1992. *Int. J Radiat Onco Biol Phys* 23, 803; Mitsutake et al. 2001 *Oncogene* 20, 989-996; Tenzer et al. 2001 *Cancer Res.* 61, 8203). PKC may be involved in several cell signaling p athways (cell survival including repair of radiation damage and cell cycle (Hallahan et al. 1992 *J Radiat Oncol Biol Phys* 24, 687), thus its inhibition may result in radiosensitization. Additionally, rapid glioma growth rate has been attributed to inherently high levels of PKC (Couldwell et al. 1990 *J Neurosurg* 73, 594; Pollack et al 1990 *J. Neurosurg.* 73, 98). Thus, identification of PKC biomarkers for brain tumorigenesis is an initial crucial step in the understanding of the progression from normal cells to benign tumors and malignant cancers. PKC is the major receptor for tumor promoting phorbol esters, but the extent of PKC involvement in cellular malignancy is not clearly defined. Various studies indicate that increased tumorigenicity results from dysregulation of PKC activity, or changes in PKC concentration, or both (Person et al. 1988 *Cell* 52, 447; Housey et al. 1988 *Cell* 52, 343; Kamata et al. 1987 *Oncogene*, 1, 37; Weyman et al. 1988 *Cancer Res.* 48, 6535; Mizuguhi et al. 1988 *Biochem. Biophy. Res. Commun.* 155,1311). Two PKC isozymes (PKC-II and PKC-iota) have been reported to be critical for some forms of cancers, including colon cancer (Gokneb-Polar et al. 2001 *Cancer Res.* 61, 1375-1381; Murray et al. 1999 *J Cell Biol* 145, 699; Murray et al. 2002 *J Cell Biol* 157, 915) and chronic myelogenous leukemia (Jamieson et al. 1999 *J. Biol. Chem.* 274, 3927; Murray et al. 1993 *J Biol. Chem.* 268, 15847; Murray & Fields 1997 *J. Biol. Chem.* 272, 27521). PKC-iota has also been shown to be overexpressed in serous and nonserous ovarian cancers through a mechanism that results in loss of apical-basal polarity and cyclin E overexpression leading to poor prognosis (Ender et al. 2005 *Proc Natl Acad Sci USA* 35,12519).

We show that PKC-iota is overexpressed in benign and malignant meningiomas and in gliomas but not in normal brain tissues. These results provide support for the involvement of PKC-iota in the transition of normal to pre-malignant and malignant lesions. Moreover, we have shown that rapidly proliferating T98G and U-138 glioma cell lines have enhanced PKC-iota compared to confluent cells. Additionally, PKC-iota siRNA reduced PKC-iota protein content and decreased cell proliferation suggesting a role for PKC-iota in regulating cell proliferation.

EXAMPLE 4

Materials and Methods

Example 4A—Brain Tissue

Human autopsy derived brain tissue and meninigiomas were obtained from the Cooperative Human Tissue Network (Southern Division) at The University of Alabama at Birmingham. Tissue specimens were obtained from both males and females of varying ages (23-80 years old). Normal brain tissue included specimens from the frontal lobe, brain cortex, cerebellum, hippocampus, pons, corpus collosum, and basal ganglia. Labeled benign tumors were meningiomas. Malignant tumors were either meningiomas or gliomas.

Example 4B—Passage of T98G and U-138 Glioma Cells

T98G and U-138 glioma cells were grown as adherent cultures. Cells were seeded into 0.22 mM filter 75 cm² flasks containing 90% MEM, 10% fetal calf serum (FCS), and antibiotics. Cells were cultured at 37° C. in a humidified atmosphere containing 5% $CO_2$ until cells become no more than 70-80% confluent. Medium is changed every other day, and replaced at a level of 5 mL medium/25 cm² growth area.

Example 4C—Inhibition of Gene Expression with siRNA

RNA interference functions by a regulatory mechanism for sequence-specific gene silencing through double stranded (dsRNA). Sequence specific RNA that was 19-25 nucleotides in length were synthesized by Santa Cruz Biotechnology against PKC-iota. PKC-iota siRNA were transfected into glioma cells (U-138 and T98G) using lipid based siRNA transfection reagent (Santa Cruz Biotechnology). The sequence-specific PKC siRNA are as follows: The PKC-iota siRNA is a pooled sequence which consists of three combined RNA sequences—mRNA location. The gene accession number for PKC-iota is NM_002740. Shown below are regions of the PKC-iota mRNA sequence with the corresponding complementary siRNA sequence immediately below.

PKC-iota siRNA

```
SEQ ID NO: 1-5'-UGUUGAAACGCUUGGCUUG-3'

SEQ ID NO: 2-5'-AUGACAACCCAAUCGUUCC-3'

SEQ ID NO: 3-5'-UACAAGAGAAGAUAUUGGG-3'
```

In addition to these siRNA, negative controls containing a scramble sequence were synthesized that do not lead to the specific degradation of any known cellular mRNA. The control siRNA-A sequence is proprietary and the Santa Cruz Biotechnology does not reveal it.

Example 4D—Cell Viability Assay

The effects of PKC-iota siRNA was determined in exponentially growing T98G or U-138 glioma cells in complete media over 72 hours. Cells were plated on 75 cm² at a density of $3.75\times10^5$ cells/flask. Twenty four hours post plating; cells were incubated with either SiRNA-A or PKC-iota siRNA (100 μM) according to manufacture's instruction (Santa Cruz Biotechnology). Following the initial exposure to siRNA no additional siRNA was neither applied nor removed during the three day incubation period. Following treatments, cells were washed with phosphate buffered saline (PBS), trypsinized and resuspended in 3 mL of PBS. Cell viability was quantified using trypan blue exclusion assay. Two hundred microliters of the cell suspension was added to 50 μl of trypan blue and the number of unstained and stained cells was counted.

Example 4E—Tissue Fractionation

Brain tissue, T98G or U-138 glioma cells were re-suspended and sonicated in 2 mL homogenization buffer (50 mM HEPES (pH 7.5) 150 mM NaCl, 0.1% Tween-20, 1 mM EDTA (ethylenediamine-tetraacetic acid) and 2 mM EGTA (ethylene glycol bis(beta-aminoethyl ether)-N,N,N',N',-tetraacetic acid), 0.1 mM orthovanadate, 1 mM NaF, 2 mM PMSF (phenyl-methylsulfonyl fluoride), 2.5 μg/ml leupeptin, 1 mM DTT (dithiothreitol), 0.15 U/mL aprotinin; Agrawal et al. 1995). The suspension was sonicated for 3 fifteen seconds cycles on ice. Brain tissue suspensions or cell lysates were centrifuged at 100,000 g for 30 min to obtain cell extracts. Protein content was measured according to Bradford 1976.

Example 4F—Cell Cycle Analysis by Flow Cytometry

Cell cycle analysis was performed as previously described (Acevedo-Duncan et al. 1997). Confluent cell cultures were either rapidly proliferating or semi-synchronized by contact inhibition and serum starvation for 48 h. Subsequently, cells were collected and washed twice with PBS and then trypsinized. The cells in the trypsin suspension were centrifuged and the trypsin decanted. To fix the cells, 3 mL of ice cold PBS was added and the cell pellet was resuspened. While vortexing gently 7 mL of ethanol was added drop wise. The day before analysis the 70% ethanol was decanted and PBTB (PBS, 0.2% Triton and 1% bovine serum albumin) was added. The cells were counted and diluted to $1\times10^6$ cells/mL with PBTB. The cells were filtered and 50 μL of RNase was added. Nuclei were analyzed for DNA content using a propidium iodine (10 μL) staining protocol and flow cytometry (Carlton et al. 1991). The distributions of 40,000 nuclei were quantified using a FAC STAR$^{Plus}$, flow cytometer (Becton Dickinson, San Jose, Calif.) and ModFitLT Cell Cycle Analysis program (Version 2.0; Verity Software House, Inc., Topsham, Me.). Statistics: Statistical determination was by Student's T test using Minitab program (Minitab Inc. State College, Pa.)

Example 4G—Western Blot Analysis

Cell extracts containing equal amounts of protein in each lane were run on SDS-PAGE gels according to Laemmli 1970. Proteins were transblotted according to Towbin et al. 1976. Brain tissue or glioma cell lysate PKC-iota was probe with monoclonal antibodies against PKC-iota (BD Transduction, Lexington). Secondary antibodies were obtained from Accurate (JOM000003, Westbury, N.Y.). Immunoreactive bands were visualized with enhanced chemiluminescence according to manufactures instructions (ECL; Amersham, Piscataway, N.J.).

Example 4H—Densitometry

The intensity of each band was measured using Gel Base/Gel Blot-Pro software (Synoptics, LTD). Briefly, the background intensity was subtracted from the intensity of each band, to derive the corrected intensity.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

SEQUENCE LISTING

<160> NUMBER OF SEQ ID NOS: 3

<210> SEQ ID NO 1
<211> LENGTH: 19
<212> TYPE: RNA
<213> ORGANISM: Artificial
<220> FEATURE:
<223> OTHER INFORMATION: small inhibiting RNA sequence for PKC iota

<400> SEQUENCE: 1
uguugaaacg cuuggcuug                                                  19

<210> SEQ ID NO 2
<211> LENGTH: 19
<212> TYPE: RNA
<213> ORGANISM: Artificial
<220> FEATURE:
<223> OTHER INFORMATION: small inhibiting RNA sequence for PKC iota

<400> SEQUENCE: 2
augacaaccc aaucguucc                                                  19

<210> SEQ ID NO 3
<211> LENGTH: 19
<212> TYPE: RNA
<213> ORGANISM: Artificial
<220> FEATURE:
<223> OTHER INFORMATION: small inhibiting RNA for PKC iota

<400> SEQUENCE: 3
uacaagagaa gauauuggg                                                  19

What is claimed is:

1. A method of detecting glioma or meningioma tumorigenesis in a subject comprising the steps of: obtaining a sample from the brain of the human subject; detecting quantitatively or semi-quantitatively in the sample a level of expression for PKC-iota; and comparing the expression level of PKC-iota to a level of expression in a normal control, wherein overexpression of PKC-iota, with respect to the control, indicates the presence of a glioma or meningioma in the subject.

2. The method according to claim 1 wherein the comparing step includes the steps of: contacting a protein sample from the brain of the subject with an antibody which recognizes PKC-iota protein; and detecting the complex between the antibody and the PKC-iota protein.

3. The method of claim 2 wherein said antibody is a monoclonal antibody.

4. The method of claim 2 wherein said antibody is a polyclonal antibody.

5. The method of claim 2 wherein said protein is contacted with said antibody in an immunoassay selected from the group consisting of radioimmunoassay, Western blot assay, immunofluorescent assay, enzyme immunoassay, immunoprecipitation, chemiluminescent assay, immunohistochemical assay, dot blot assay and slot blot assay.

6. The method of claim 3 wherein said immunoassay is a Western blot assay.

7. A method of detecting glioma or meningioma tumorigenesis in a subject comprising the steps of: obtaining a sample from the brain of the human subject; detecting quantitatively or semi-quantitatively in the sample a level of expression for PKC-iota; and comparing the expression level to a level of expression in one or more controls wherein the controls are selected from the group consisting of a negative brain tissue control, a positive brain tissue control and combinations thereof.

* * * * *